United States Patent
Hadimioglu et al.

(10) Patent No.: US 6,503,454 B1
(45) Date of Patent: Jan. 7, 2003

(54) MULTI-EJECTOR SYSTEM FOR EJECTING BIOFLUIDS

(75) Inventors: Babur B. Hadimioglu, Mountain View, CA (US); Scott A. Elrod, La Honda, CA (US); Richard H. Bruce, Los Altos, CA (US); Jaan Noolandi, Mississauga (CA); David A. Horine, Los Altos, CA (US)

(73) Assignee: Xerox Corporation, Stamford, CT (US)

( * ) Notice: Subject to any disclaimer, the term of this patent is extended or adjusted under 35 U.S.C. 154(b) by 190 days.

(21) Appl. No.: 09/721,389

(22) Filed: Nov. 22, 2000

(51) Int. Cl.$^7$ .............................. B01L 3/02; G01N 1/10; B41J 2/145; B41J 2/135; B41J 2/14; B41J 2/16; B41J 2/045

(52) U.S. Cl. ........................ 422/100; 436/180; 347/40; 347/44; 347/47; 347/48; 347/50; 347/51; 34/68; 34/71

(58) Field of Search ................................. 422/100, 102, 422/99; 436/180; 347/48, 51, 40, 44, 68, 71, 72, 50, 55, 54

(56) References Cited

U.S. PATENT DOCUMENTS

| | | | |
|---|---|---|---|
| 5,565,113 A | 10/1996 | Hadimioglu et al. | |
| 5,631,678 A | 5/1997 | Hadimioglu et al. | |
| 5,699,098 A | * 12/1997 | Matsuda et al. | ............. 347/171 |
| 5,828,391 A | * 10/1998 | Shinozaki et al. | .......... 347/171 |
| 5,847,732 A | * 12/1998 | Shinozaki et al. | ............. 347/51 |
| 6,114,122 A | 9/2000 | Besemer et al. | |
| 6,244,688 B1 | * 6/2001 | Hickman | ..................... 347/15 |
| 6,447,097 B1 | * 9/2002 | Folkins et al. | ................. 347/12 |
| 2001/0043243 A1 | * 11/2001 | Tachihara et al. | ............. 347/15 |
| 2001/0048452 A1 | * 12/2001 | Lan et al. | ...................... 347/42 |

OTHER PUBLICATIONS

Experts in Microdispensing & Precision Printing (MicroFab Technologies, Inc.) http://www.microfab.com—last updated Jun. 12, 2000.

* cited by examiner

Primary Examiner—Jill Warden
Assistant Examiner—Brian R Gordon
(74) Attorney, Agent, or Firm—Fay, Sharpe, Fagan, Minnich & McKee, LLP

(57) ABSTRACT

A multiple-ejector system for printing arrays of biofluids include a tooling plate having a plurality of sets of tooling pins extending outward from the surface of the tooling plate. A printed circuit board is provided having pairs of power connection pins and ground return pins extending from a surface of the circuit board. A plurality of biofluid drop ejection units are provided and include alignment grooves and at least a transducer. Each of the plurality of biofluid drop ejection units are connected to a corresponding one of a set of tooling pins by connection of the tooling pins and alignment grooves. The power connection pins of the pairs are in operational connection with respective transducers and the ground return connection pins of the pairs are in operational connection with a body portion of the drop ejection units. The different drop ejection units will contain different biofluids which are to be emitted onto a substrate. Verification of drop ejection units containing biofluids, may be obtained in one embodiment through the use of an optical scanner. Detection of drops at defined locations provides a verification that validates a properly formed spot is present on a substrate, and is in the correct position.

**16 Claims, 16

MULTI-EJECTOR SYSTEM FOR EJECTING BIOFLUIDS

BACKGROUND OF THE INVENTION

The present invention is directed to multiple ejector systems implementing a plurality of biofluid ejectors arranged to print biological assays.

Many scientific tests such as those directed to biology, genetics, pharmacology and medicine, employ sequences or arrays of biofluid drops upon which the tests are to be performed. In some testing applications up to several thousand biofluid drops are deposited onto a single substrate where a single substrate contains a variety of unique biofluids. For example, in current biological testing for genetic defects and other biochemical aberrations, thousands of the individual biofluids may be placed on a glass substrate at different locations. Thereafter, additional biofluids may be deposited on the same locations to obtain an interaction. This printed biological assay is then scanned with a laser in order to observe changes in a physical property.

In these situations it is critical that the drop ejection devices not be a source of contamination or permit cross-contamination between biofluids. Another consideration in the printing of biological assays is the high cost of the biofluids used in such experiments. It is therefore desirable to minimize the volume of biofluid required for generating a biological assay.

Existing mechanisms used to produce biological assays fall short in their ability to accurately place the biofluid drops such as to avoid contamination and cross-contamination. They also use larger volumes of biofluid than desirable, and use processes to form the biological assays which are time intensive.

It has therefore been considered desirable to develop multiple ejector systems which emit biofluids in a manner that avoids contamination and cross-contamination, uses small volumes of biofluids in the printing process, and has a high throughput which makes the printing of the biological assays highly efficient and economical.

SUMMARY OF THE INVENTION

A multiple-ejector system for printing arrays of biofluids include a tooling plate having a plurality of sets of tooling pins extending outward from the surface of the tooling plate. A printed circuit board is provided having pairs of power connection pins and ground return pins extending from a surface of the circuit board. A plurality of biofluid drop ejection units are provided and include alignment grooves and a transducer. Each of the plurality of biofluid drop ejection units are attached to a corresponding one of a set of tooling pins by connection of the tooling pins and alignment grooves. The power connection pins are placed in operational engagement with respective transducers, and the ground return connection pins are in operational engagement with a body portion of the drop ejection units. The drop ejection units contain different biofluids which are to be emitted onto a substrate. Verification of drop ejection units containing biofluids, may be obtained in one embodiment through the use of an optical scanner. Detection of drops at defined locations, provides a verification that validates a properly formed spot is present on a substrate, and is in the correct position.

DETAILED DESCRIPTION OF PREFERRED EMBODIMENTS

Figure 1:
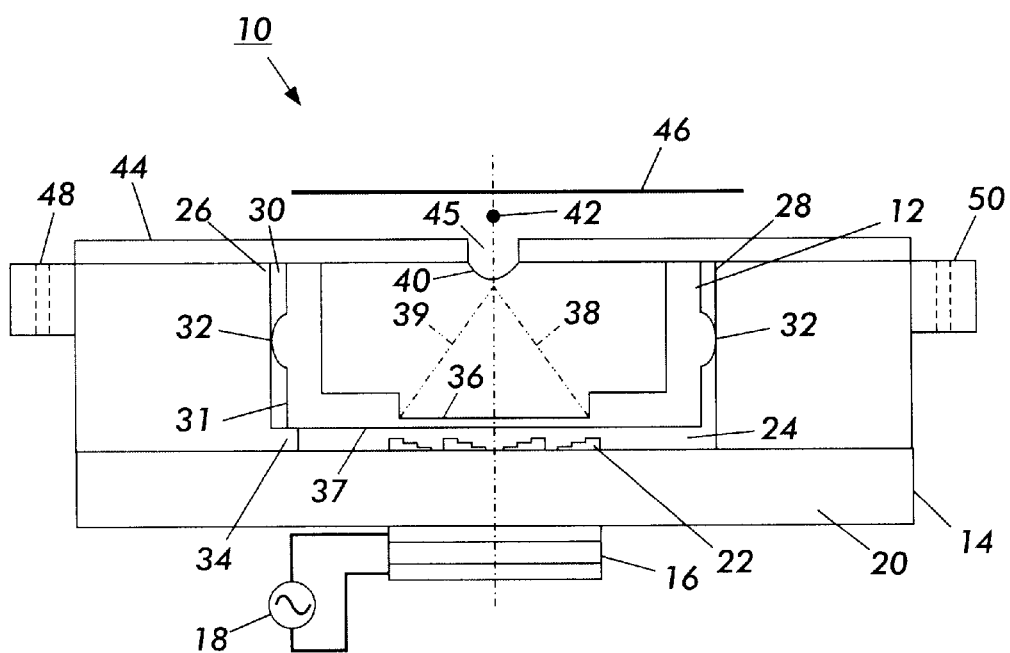
FIG. 1 sets forth a cross-sectional view of the reagent cartridge inserted within an acoustic drop ejection mechanism.
Figure 2:
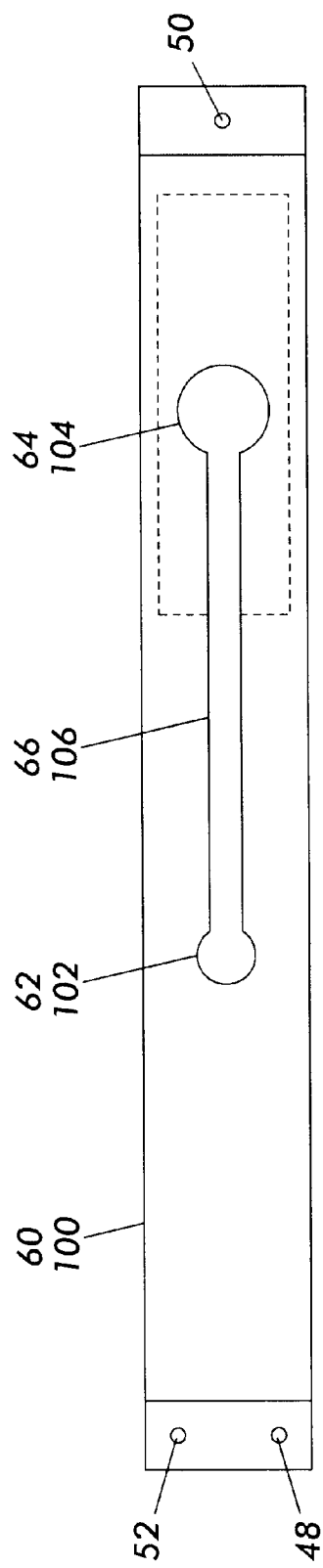
FIGS. 2 and 3 are respective top and side views of an alternative single piece acoustic drop ejection mechanism.
Figure 3:
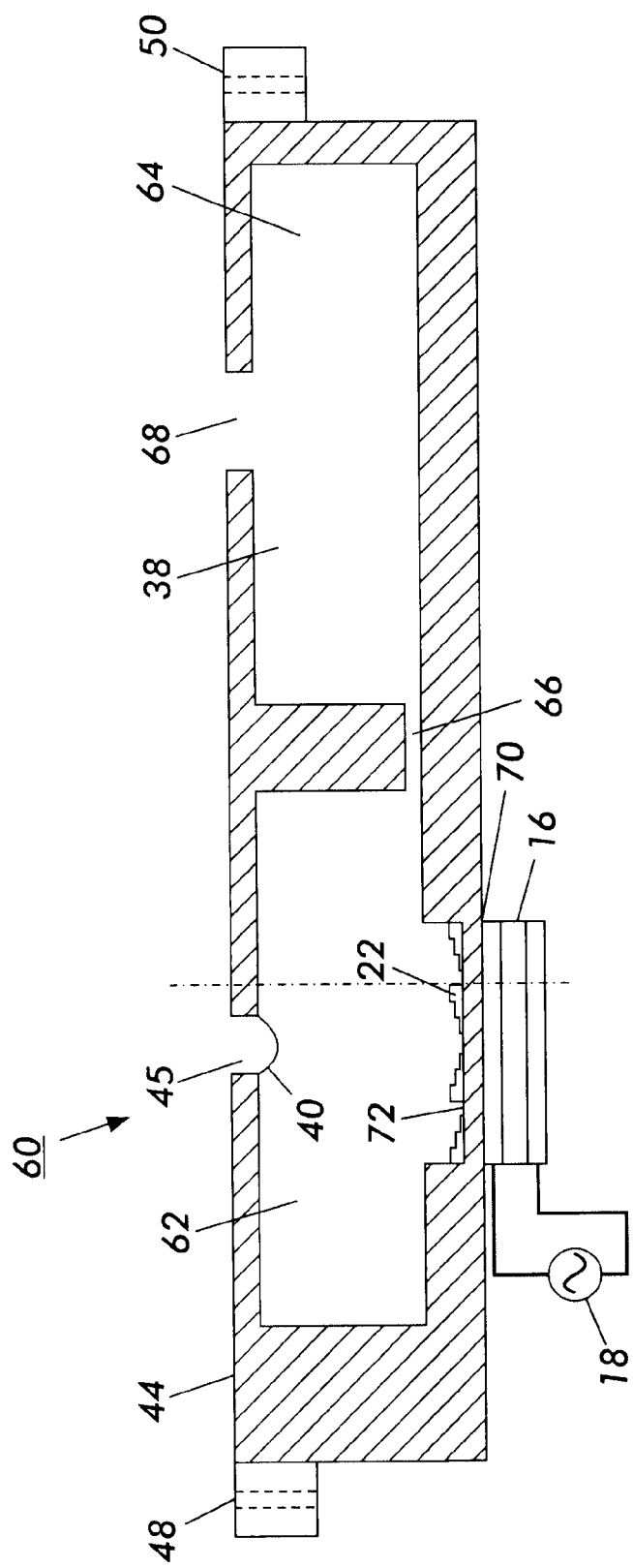
Figure 4:
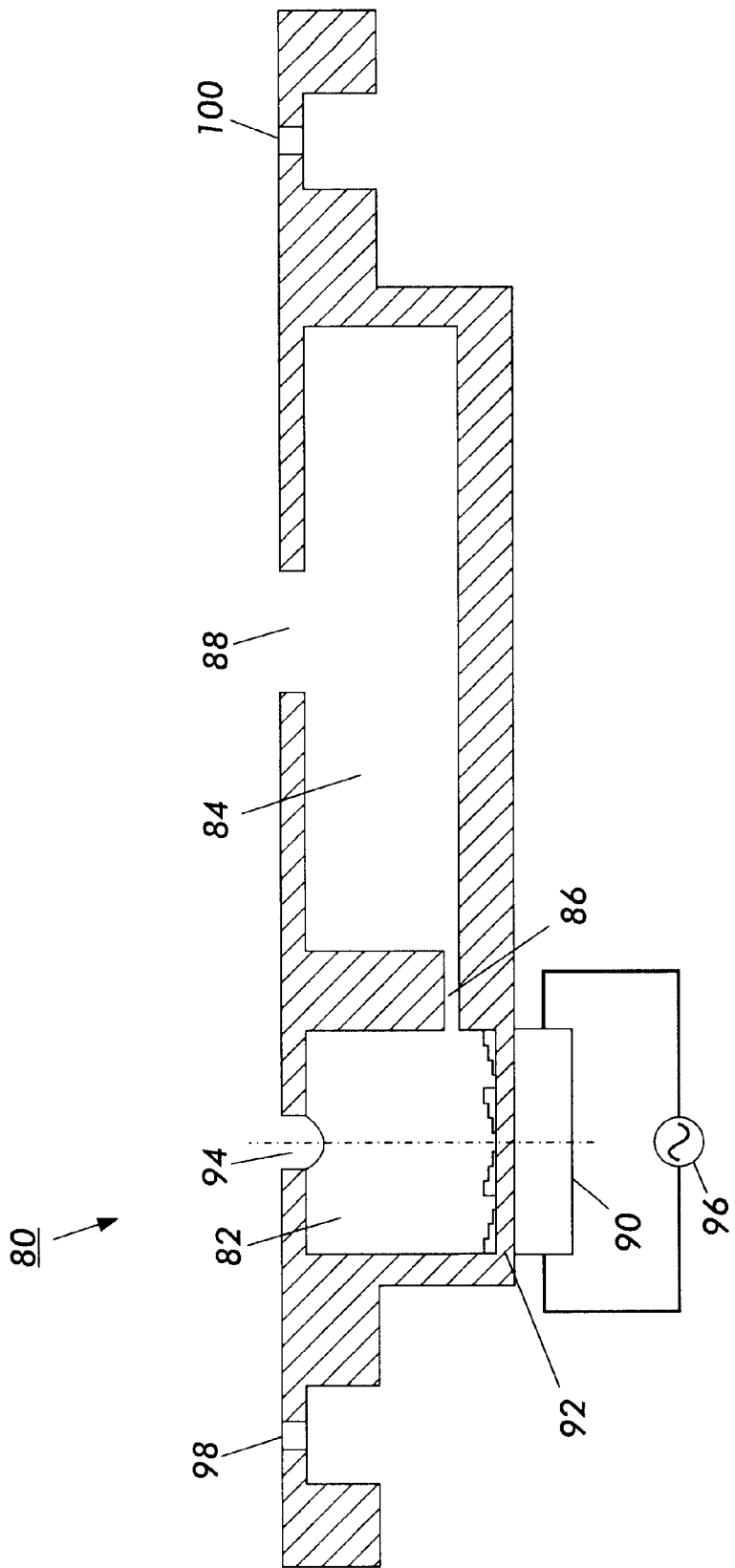
FIGS. 4 and 5 depict a single piece piezoelectric drop ejection mechanism.
Figure 5:
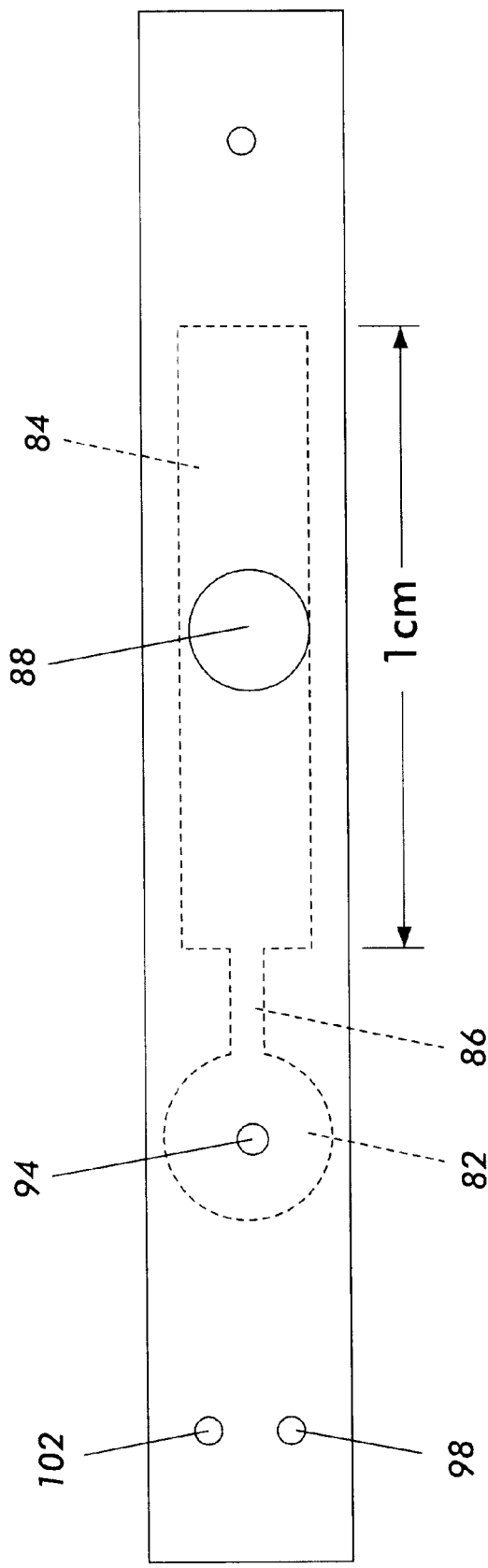

FIG. 1 depicts a cross-sectional view of a drop ejection system 10 including single reagent cartridge 12 inserted within a single acoustic drop ejection mechanism 14. A transducer 16 is supplied with energy by power supply source 18. Transducer 16 is provided on a surface of substrate 20, which in one embodiment may be made of glass. Patterned or located on an opposite surface of substrate 20 is a focusing lens configuration 22 such as a Fresnel lens. It is to be appreciated that other types of focusing configurations may also be used in place of the Fresnel lens.

An acoustic coupling layer 24, which may be an acoustic coupling fluid, is located between Fresnel lens 22 and reagent cartridge 12. The acoustic coupling fluid 24 is selected to have low acoustic attenuation. One type of acoustic coupling fluid having beneficial acoustic characteristics for this application is water. In an alternative embodiment, connecting layer 24 may be a thin layer of grease. The grease connection will be useful when the joining surfaces are relatively flat in order to minimize the possibility of trapped bubbles.

On top of substrate 20 are walls 26, 28 which define interior chamber 30 within which reagent cartridge 12 is located. Side wall 31 of cartridge 12 includes a seal 32 extending from its outer surface. Seal 32 secures cartridge 12 within chamber 30 and maintains acoustic coupling fluid 24 below seal 32. A precision depth stop 34 holds cartridge 12 at a desired insertion location. A thin membrane 36 is formed on a lower surface 37 of cartridge 12, positioned substantially above Fresnel lens 22. Membrane 36 is an acoustically thin membrane, wherein acoustically thin is defined in this context to mean that the thickness of the membrane is small enough that it passes over 50% of its incident acoustic energy through to biofluid 38 within cartridge 12.

In operation, energization of transducer 16 emits an acoustic wave which travels through substrate 20 to Fresnel lens 22. The lens produces a focused acoustic energy wave 39 that passes through acoustic coupling fluid 24 and membrane 36, reaching an apex at biofluid meniscus surface 40 of biofluid 38. Supplying of the focused energy to surface 40 causes disruptions in the surface, resulting in ejection of a biofluid drop 42 from the cartridge 12 to substrate 43. The biofluid drop ejected can be as small as approximately 15 um in diameter. However, this size limitation is based on the physical components used, and it is to be understood that drops ejected by an acoustic drop ejection unit can be made smaller or larger in accordance with design changes to the physical components.

The surface from which biofluid drops 42 are ejected can be either totally open or contained by an aperture plate or lid 44. The lid 44 will have a suitably sized aperture 45, which is larger than the ejected drop size in order to avoid any interference with drop ejection. Aperture 45 must be sized so that the surface tension of meniscus 40 across aperture 45 sufficiently exceeds the gravitational force on biofluid 38. This design will prevent biofluid 38 from falling from regent cartridge 12 when cartridge 12 is turned with aperture 45 facing down. The aperture down configuration has a benefit of maintaining the biofluid 38 clean from material which may fall from substrate 46, which may be paper, glass, plastic or other appropriate material.

The foregoing design isolates biofluid 38 within reagent cartridge 12, preventing it from coming into contact with drop ejection mechanism 14, or other potential forms of contamination, such as airborne contamination or contamination from biofluids previously used with the ejection mechanism. Reagent cartridge 12 is separated from acoustic coupling fluid 24 by membrane 36. The entire cartridge may be injection molded from a biologically inert material, such as polyethylene or polypropylene. Cartridge 12 is operationally linked to the acoustic drop emitter mechanism 14 by a connection interface which includes membrane 36 and acoustic coupling fluid 24.

In a specific design of the present invention, the diameter of the transducer and the lens is approximately 300 microns, and membrane 36 may be 3 microns thick. In this particular embodiment, with a design constraint of a focal length being approximately 300 microns and at an operating frequency of approximately 150 mHZ for known acoustic drop ejection mechanisms, the meniscus location should be maintained within plus or minus 5 microns from an ideal surface level.

Power source 18 is a controllably variable. By altering the output of power source 18, energy generated by transducer 16 is adjusted, which in turn may be used to alter the volume of an emitted biofluid 42.

Figure 6:
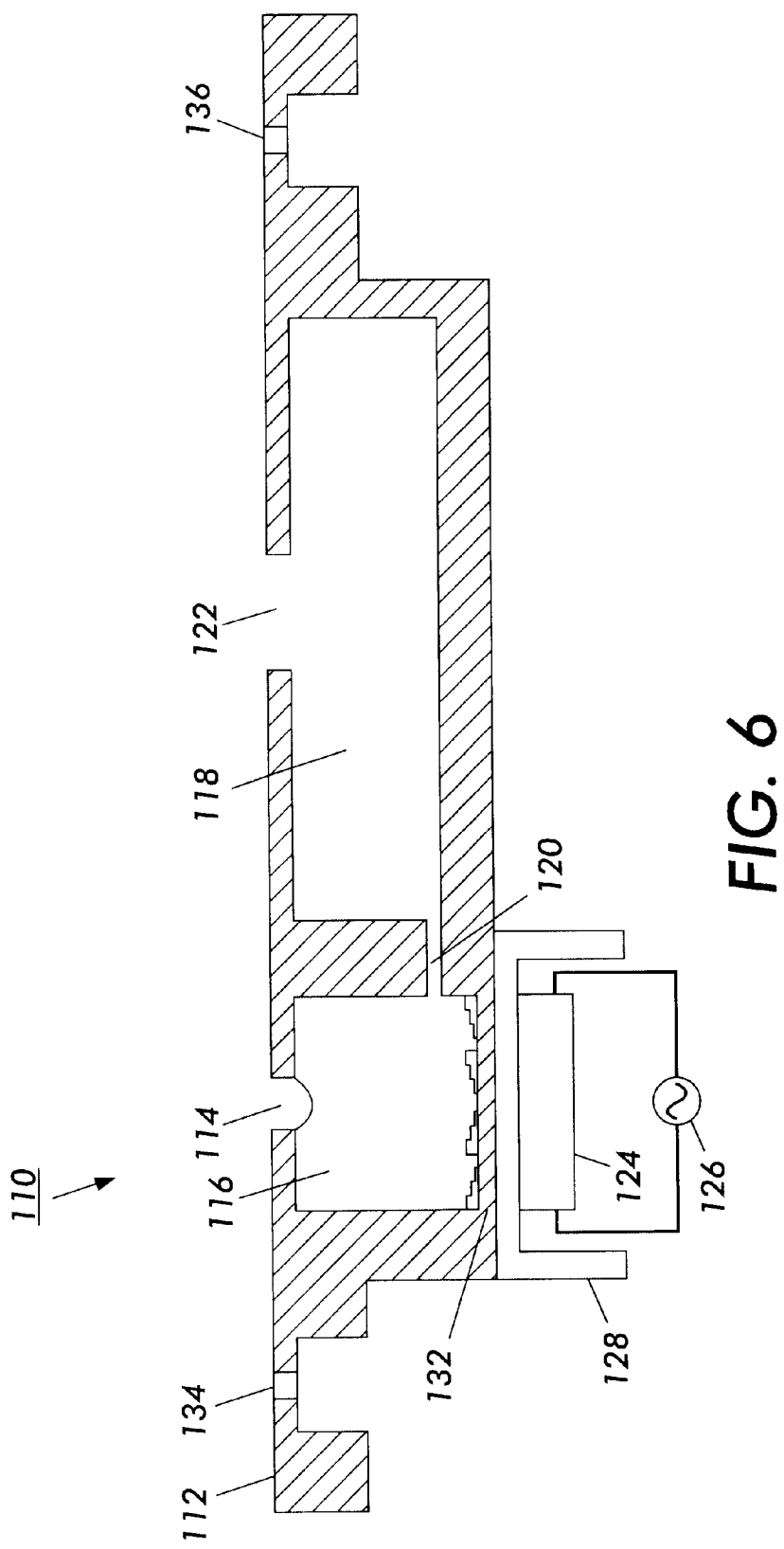
FIGS. 6 and 7 illustrate a two piece piezoelectric drop ejection mechanism.
Figure 7:
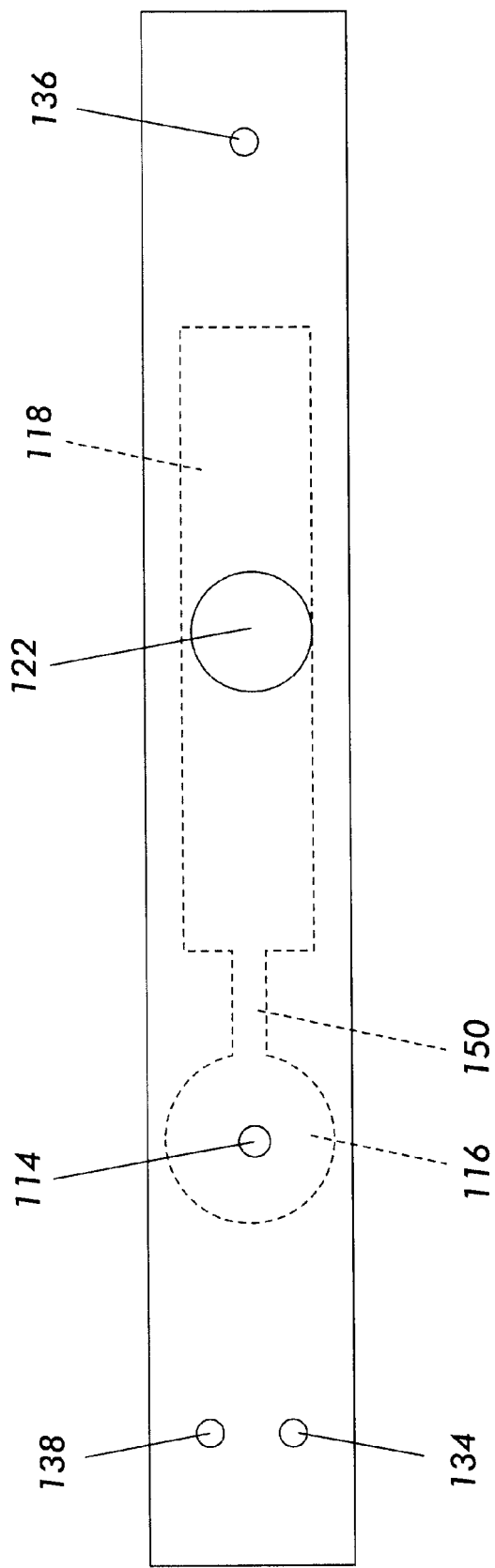

Alignment grooves 48, 50 which are grooved holes, are formed during the same lithographic process which forms acoustic drop ejection unit 10. These alignment members are used when the individual ejector unit 10 is inserted within a multiple ejector system as will be described in following sections of this discussion. It is noted that a third alignment member behind alignment groove 48 is not shown.

Turning to FIGS. 2 and 3, illustrated is a single piece acoustic drop ejection unit 60. In this figure, ejection reservoir 62 and main reservoir 64 are placed in fluid communication by reservoir connect 66. Capillary action assists in pulling biofluid from main reservoir 64 to ejection reservoir 62, in an initial filling operation when main and ejection reservoirs are empty. However, once the unit is primed and filled to the bottom of aperture 45, a restoring force/surface tension of meniscus 40 is used to pull the biofluid from the main reservoir 64 to the ejection reservoir 62 as drops are ejected. To provide sufficient surface tension at the aperture 45, it is important to have aperture 45 much smaller than filling port 68, so as to avoid a competitive surface tension of filling port 68. The surface tension force of aperture 45 must also be larger than the gravity effect over the height of the structure. By properly balancing these forces, the aperture surface tension continues pulling biofluid into the ejection reservoir 62, to maintain it full, until the main reservoir 64 is depleted.

In FIGS. 2 and 3, transducer 16 is shown in operational connection to a first surface of substrate 70, and lens arrangement 22 is integrated on a second surface of membrane 72, whereby these components are formed as part of the single unit 60. In this embodiment, a connecting layer 24 of FIG. 1 is not required due to the single component disposable nature of the present embodiment. In ejection reservoir 62, biofluid 38 comes into direct contact with lens arrangement 22. Main reservoir 64 is filled through filling port 68. Alignment grooves 48, 50, 52 are shown in FIG. 2.

Turning to FIGS. 4 and 5, set forth are side and top views of a single piece disposable piezoelectric drop ejection unit 80. Ejection reservoir 82 is connected to main reservoir 84 via reservoir connect 86. Biofluid is supplied to main reservoir 84 via filling port 88. A piezo actuator 90 is in operational connection to a lower surface 92 of ejection reservoir 82. An upper surface defining the ejection reservoir 82 has formed therein an ejection nozzle 94. A power supply 96 is connected to piezo actuator 90. Alignment grooves 98, 100, 102 are formed during the same process which forms ejection nozzle 94. The resulting integral relationship results in a highly precise placement of unit 80 in a multiple ejection system.

In operation piezo actuator 90 is actuated by power supply 96, which in combination with lower surface 92 comprises a unimorph configuration which generates a deflection force in response to an applied voltage. The deflection force is imposed such that the unimorph configuration moves into ejection reservoir 82, thereby altering the volume of ejection reservoir 82, which in turn forces biofluid from the ejection reservoir 92 through nozzle 94 as an ejected biofluid drop. The size of nozzle 94 is a controlling factor as to the size of the ejected drops.

As biofluid drops are emitted from ejection reservoir 82, surface tension in the ejection reservoir causes biofluid located in main reservoir 84 to be drawn through reservoir connect 86 into ejection reservoir 82, thereby replenishing the biofluid level. Similar to previous discussions, sufficient surface tension is obtained by taking into account the size of filling port 88 and the effect of gravity over the height of the structure. In the present embodiment, main reservoir 84 has an internal dimension of 1 cm in length and 2.5 mm in height. The width of the overall piezoelectric drop ejection unit is 5 mm, as shown in FIG. 5. This small size allows for the aggregation of large numbers of ejectors in a system configuration to print multiple biofluids.

As can be seen in FIG. 4, lower surface 92 connected to piezo actuator 90 is integrated into the overall piezoelectric drop ejector unit 80. Under this construction when biofluid of unit 80 is depleted the entire unit 80 may be disposed.

FIGS. 6 and 7, show side and top views of a two piece piezoelectric biofluid drop ejection unit 110 having a disposable portion and a reusable portion. The disposable portion includes a reagent cartridge 112 which has integrated therein an ejection nozzle 114, and an ejection reservoir 116, connected to a main reservoir 118 via a reservoir connect 120. Transmission of biofluid from main reservoir 148 to ejection reservoir 116, via reservoir connect 120 occurs by a capillary feed action. Also included is a filling port 122. The reusable portion of unit 110 includes actuator 124 powered by a power supply source 126. The piezo actuator 124 is carried on a reusable frame 128.

A flexible membrane lower surface 130, such as a thin layer of polyethylene, polyimide, or other thin plastic, defines a portion of the ejection reservoir 116 and is bonded to diaphragm upper surface 132 of reusable frame 128. Diaphragm 132, which in one embodiment may be stainless steel, is bonded or otherwise connected to piezo actuator 124 such that diaphragm 132 acts as part of a unimorph structure to create a necessary volume change within ejection reservoir 116 in order to eject a biofluid drop from ejection nozzle 114. Flexible membrane 130 of cartridge 112 acts to transfer the volume change in the reusable portion 128 into the disposable portion. Alignment grooves 134, 136, 138 are formed during the same process which is used to form ejection nozzle 114. The resulting integral relationship results in a highly precise placement of unit 110 in a multiple ejector system.

The disclosed biofluid drop ejection units will function using small amounts of biofluid within the main reservoir and the ejection reservoir. For example, the main reservoir may in one instance, when full, contain anywhere from 50 to 150 microliters of biofluid where the ejection reservoir, when full, holds anywhere from 5 to 25 microliters. Thus, it can be seen that operation of the described ejector units are possible using very low volumes of biofluid. The biofluid drops themselves may be in the picoliter range. This is a valuable aspect of these ejector units due to the high cost for many of the biofluids which will be used. Also, since very small volumes of biofluid are required, the use of disposable ejector units become an attractive option.

It is to be appreciated that the described units also operate at a high efficiency whereby little waste of the biofluids will occur. This is both due to the operational aspects of the units themselves and to the fact that small volumes of biofluid are necessary to operate the units. Particularly, if any waste does exist within the system, due to the small amount of biofluid originally used, high efficiencies in operation are nevertheless achievable. In one preferred embodiment high efficiency is defined as use of 80% or more of the biofluid under normal operation.

While the foregoing discussion stated there would be 50–150 microliters in the main reservoir, and 5–25 microliters in the ejection reservoir, these amounts may vary dependant on the drop size being used, the amount of printing to be undertaken, the types of biofluids to be used, as well as other parameters.

A ratio from 2 to 1 to a 10 to 1 of biofluid volume in the main reservoir and the ejector reservoir is a preferred range. This range permits usable surface tension for the drawing of biofluid in certain disclosed embodiments, while also using the small volumes desired. However, it is possible that larger ratios may also be used dependent upon factors including the cost of the biofluid, and the intended use of the ejectors.

Figure 8:
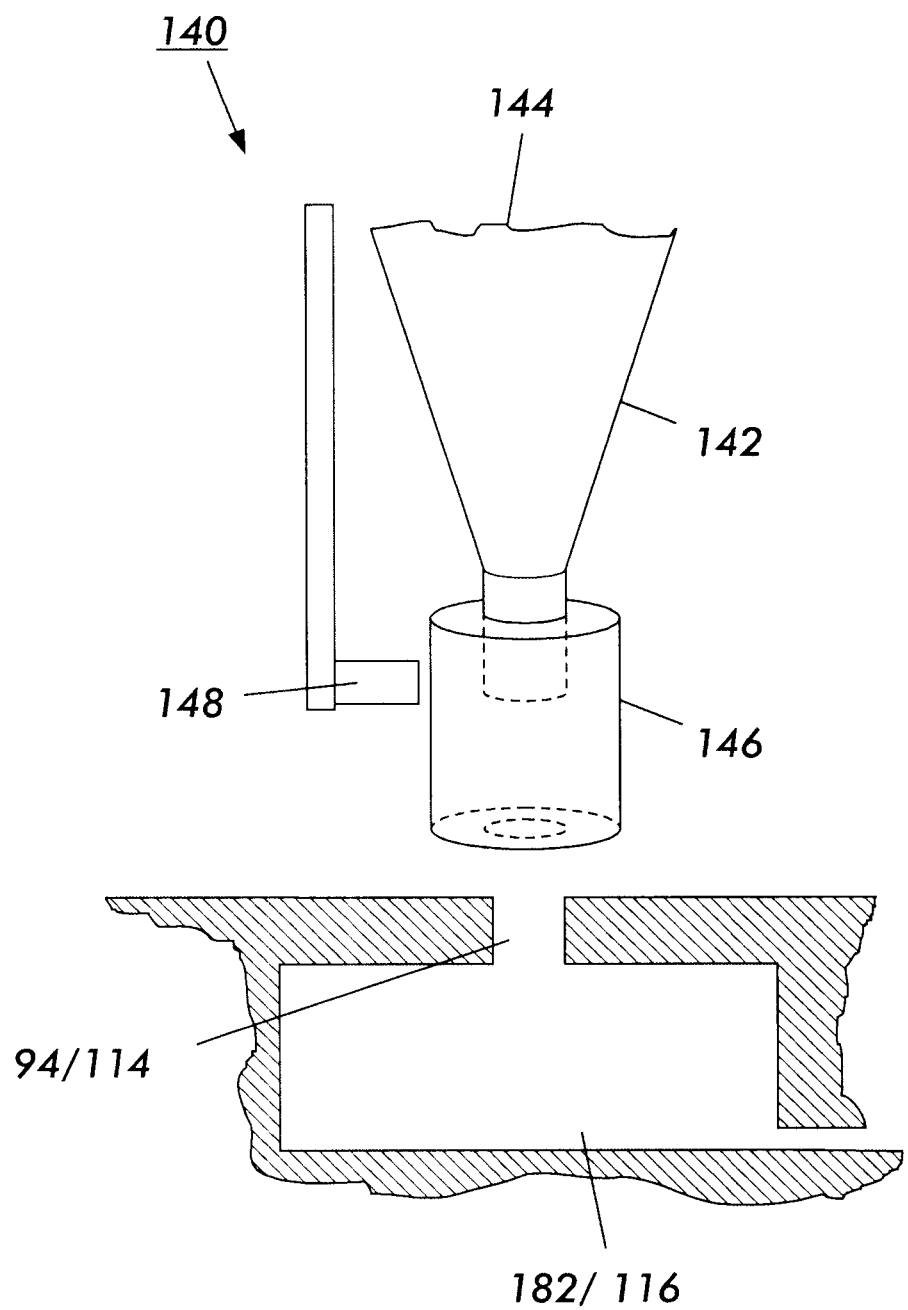
FIG. 8 sets forth a disposable primer connection used in connection with the single and two piece piezoelectric drop ejection mechanisms.
Figure 16:
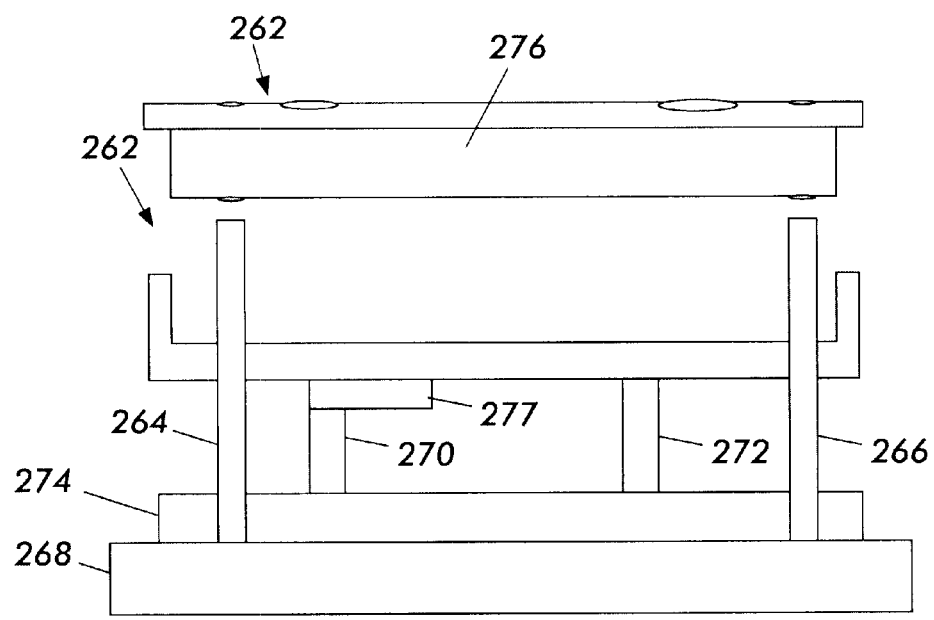

FIG. 8 illustrates a primer connection 140 which may be used in accordance with the present invention. As shown in FIG. 16, the primer connection 140 is located over a nozzle (94, 114) which is configured to emit biofluid from an ejection reservoir (82, 116). In operation, primer connection 140 may be a robotically actuated device which moves over an ejection nozzle (94/114). The primer connection 140 includes a permanent nozzle 142 connected to a vacuum unit 144. Placed around permanent nozzle 142 is a disposable tubing 146 made of an elastomaric or other suitable connection material. Once located over ejection nozzle (94, 114), the vacuum nozzle 142 is moved downward, placing the disposable tubing 146 into a loose contact with nozzle (94, 114). Vacuuming action vacuums air out of the ejection reservoir (82,116). A liquid height detection sensor 148 determines when the biofluid has reached a level within the disposable tubing (94, 114), such that it is insured air within the ejection reservoir has been removed. This priming operation permits proper initial drop ejection operation.

Other embodiments of biofluid drop ejection mechanisms and fluid control devices are described in U.S. patent application Ser. No. D/A0879, entitled DEVICES FOR BIOFLUID DROP EJECTION, and U.S. patent application Ser. No. D/A0880, entitled LEVEL SENSE AND CONTROL SYSTEM FOR BIOFLUID DROP EJECTION DEVICES, assigned to the present assignee and hereby incorporated by reference.

As noted previously, an intended use for the described drop ejection mechanisms are to print biological assays containing large numbers of different biofluid drops. The following discussion focuses on a biological printing system employing numerous drop ejection units of the type just described, whereby the system is capable of printing arrays of different biological materials such as DNA and proteins.

Figure 9:
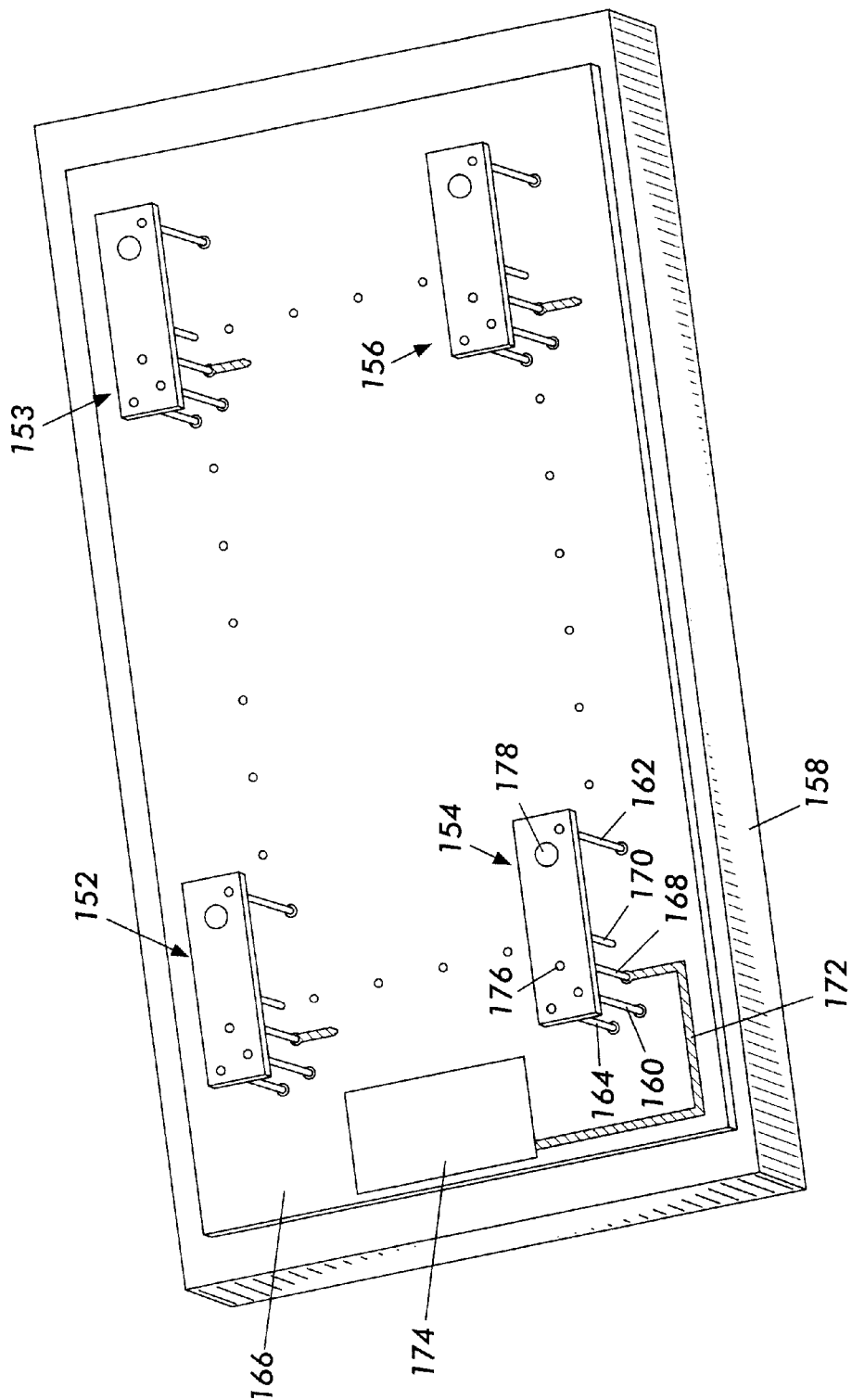
FIG. 9 illustrates a multiple ejector system which may implement either single or double piece piezoelectric and acoustic drop ejection mechanisms.

FIG. 9 illustrates a multiple ejector system (MES) 150 which permits the printing of high density biological assays. Multiple ejector system 150 of this embodiment consists of an array having 10 rows, where each row includes 100 drop ejector units. Particularly, in this embodiment drop ejector unit 152 may be considered a first ejector in a first row. Drop ejector 153 is the $100^{th}$ ejector in the first row, ejector 154 is the first ejector in the $10^{th}$ row and ejector 156 is the $100^{th}$ ejector in the $10^{th}$ row. For convenience, only selected ones of the 1,000 ejectors of this array are shown. It is to be understood that multiple ejector systems having a different number of ejectors are also obtainable using the present concepts.

Configuration of MES 150 includes a tooling plate 158 which has machined therein sets of conical-tip tooling pins 160, 162 and 164. These tooling pins are precisely manufactured into the tooling plate to selectively engage alignment grooves (48–52, 98–102, and 134–138) of FIGS. 1–7. Use of tooling pins 160–164 ensures appropriate registration of the nozzle of the piezoelectric drop ejection units or the aperture of the acoustic drop ejection units. It is to be appreciated that drop ejection units 152–156 are intended to represent either piezoelectric or acoustic drop ejection units.

Tooling plate 158 may be made of steel or other appropriate material. Placed on a top or first surface of tooling plate 158 is a printed circuit board 166. Extending from the surface of PC board 166, are power connection pin 168 and a ground return connection pin 170. The connection pins 168 and 170 engage the drop ejection unit 154 on one end and the printed circuit board on a second end. Additionally, power connection pin 168 is further connected to an electrical trace 172 located on the PC board 166, which in turn connects to a controller or driver chip 174. The controller or driver chip 174 selectively supplies power to drop ejection unit 154 via electrical trace 172 and power connection pin 168. As will be discussed in greater detail below, this selective application of power is used to operate drop ejection unit 154.

As shown, drop ejection unit 154 will include either a nozzle or aperture 176, dependent upon whether the mechanism is a piezoelectric drop ejection unit or an acoustic drop ejection unit. A fill port 178 is provided for the receipt of a biofluid used to print the biological assay. It is to be appreciated that different biofluids will be placed in different ejectors of the multiple ejector system 150. By proper placement of the tooling pins 160–164, and the placement of the alignment grooves, overall placement of individual drop ejector units with the system 150 may be ensured to within a thousandth of an inch of an ideal location.

Figure 10:
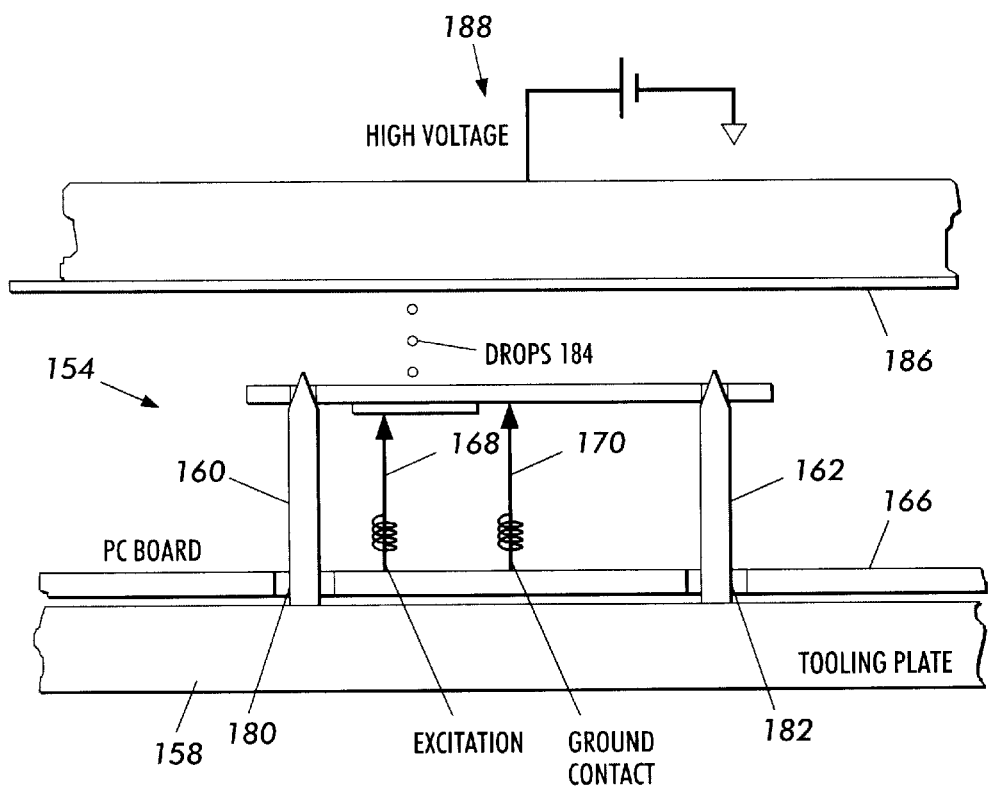
FIG. 10 sets forth a side view of a multiple ejector system illustrating a single ejector, single piece mechanism.

Turning to FIG. 10, illustrated is a side view of a single drop ejection unit 154 of multiple ejector system 150. Tooling plate 158 includes the tooling pins 160 and 162 previously described. Pin 164 cannot be viewed in this figure, as it is located behind pin 160. On top of tooling plate 158 is PC board 166 having through holes 180 and 182. A further throughhole for pin 164 would also be provided. As shown more clearly in this figure, connection pins 168 and 170 extend from the surface of PC board 166 to engagement at appropriate locations of drop ejection unit 154. For example, connection pin 168 which receives power from controller 174, operationally engages the transducer of either the piezoelectric or acoustic drop ejection unit. Supplying power activates the drop ejection unit causing emission of drops 184. A ground contact is achieved by use of connection pin 170. Both connection pins 168 and 170 may be designed as pogo pins which are a spring-loaded mechanism. Thus when drop ejection unit 154 is located over tooling pins 160, 162, 164 and is pressed downward such that pins 160–164 pass through corresponding alignment holes, spring engagement is made between connection pins 168, 170 and drop ejection unit 154 providing the electrical contacts described.

A static voltage 188 may be placed on the backside of substrate 186 to counter the affects of gravity and viscous drag on drops 184, which act to move drops out of a straight path to the substrate. Use of static voltage 188 increases the accuracy with which drops 184 are placed on substrate 186, by providing a strong attraction force. The flight of the drops are an important concept as small misregistrations can cause cross-contamination between drops or misreadings of the biological assay once developed.

Figure 11:
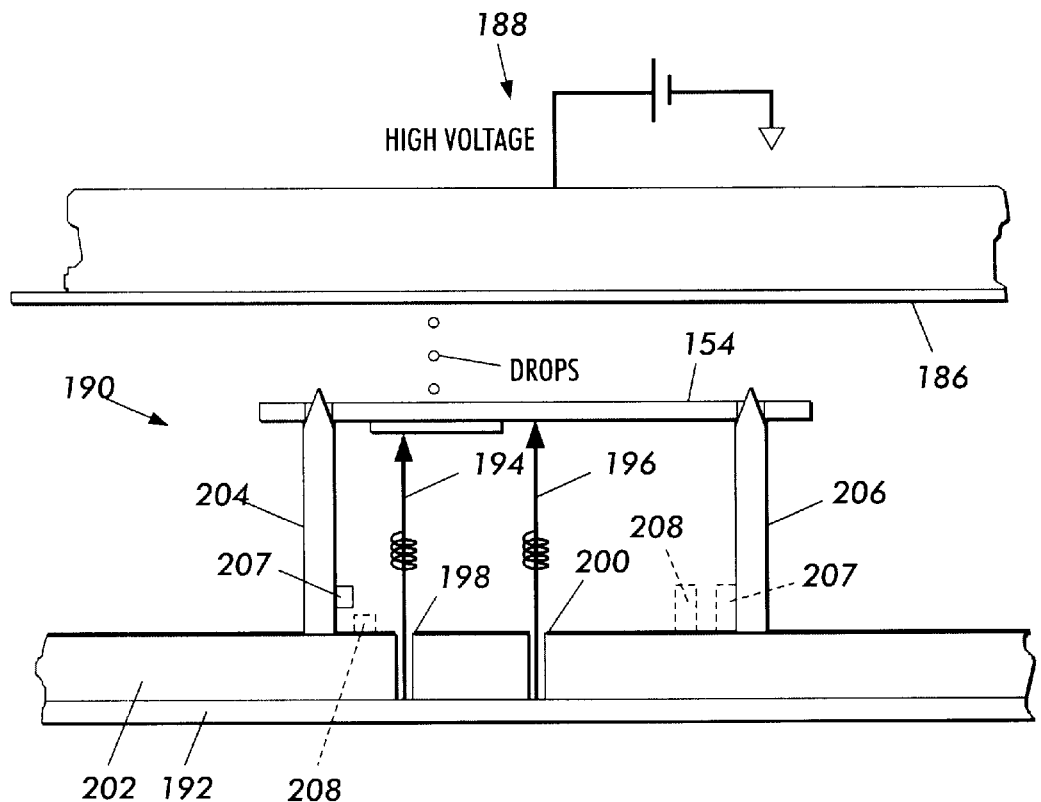
FIG. 11 sets forth a second embodiment of a multiple ejector system wherein shown is a single ejector.

FIG. 11, is a side view of a selected drop ejector 154 from an alternative multiple ejector system 190. In this embodiment circuit board 192 is the lowermost element of MES 190. Power connection pin 194 and ground return connection pin 196 are passed through openings 198 and 200 of tooling plate 202. It is to be noted that openings 198 and 200 need to be electrically isolated from pins 194 and 196. Similar to the previous discussion, tooling plate 202 has multiple sets of tooling pins 204 and 206 extending from the surface of tooling plate. It is noted that a third tooling pin of the set, such as shown in FIG. 9 is also provided in FIG. 11 though not shown. Thereafter, drop ejection unit 154 is placed into engagement with tooling pins 204, 206 and connection pins 194, 196 in a similarly described manner.

While the forgoing discussion has focused on tooling pins of FIGS. 10 and 11 as being conical pins on which the drop ejector 154 rests, in an alternative embodiment, these tooling pins may be designed simply to pass through the drop ejector and the drop ejector will move down until hitting predetermined stops located either extending from the pins themselves or from the tooling plate, such as stops 207 or 208, shown in dashed lines. Stops 207 and 208 are positioned such that proper alignment of the drop ejector is achieved. If this embodiment is undertaken, then tooling pins, such as 204 and 206 may be made much shorter in length. The shortening of the tooling pins are made shorter such that the portions of the pins passing through the drop ejector do not extend into the printing plane. In the embodiment shown in FIG. 11, the stops may also be provided by the PC board 166.

With attention to a further embodiment of the devices shown in FIGS. 10 and 11, while 2 connection or pogo pins 168, 170 in FIG. 10 and 194, 196 in FIG. 11, are shown to provide an excitation and a ground return, an embodiment with a single pogo pin may also be used. In the single pogo pin embodiment, the excitation pins 168 or 194 of FIGS. 10 and 11 will be maintained. However, the return or ground contact pogo pins 170 and 196 of FIGS. 10 and 11 may be replaced by providing the ground contact through use of the tooling pins interconnected to the alignment openings.

Multiple ejector systems 150, 190, may be considered most applicable to single-piece drop ejection units. When these drop ejection units have been exhausted of biofluid, they may be removed from the tooling pins and replaced with new ejection units. Removal of the drop ejection unit from the tooling pins may be accomplished by any of many known designs such as a snap-fit connection which is releasable upon application of an upward pressure.

Figure 12:
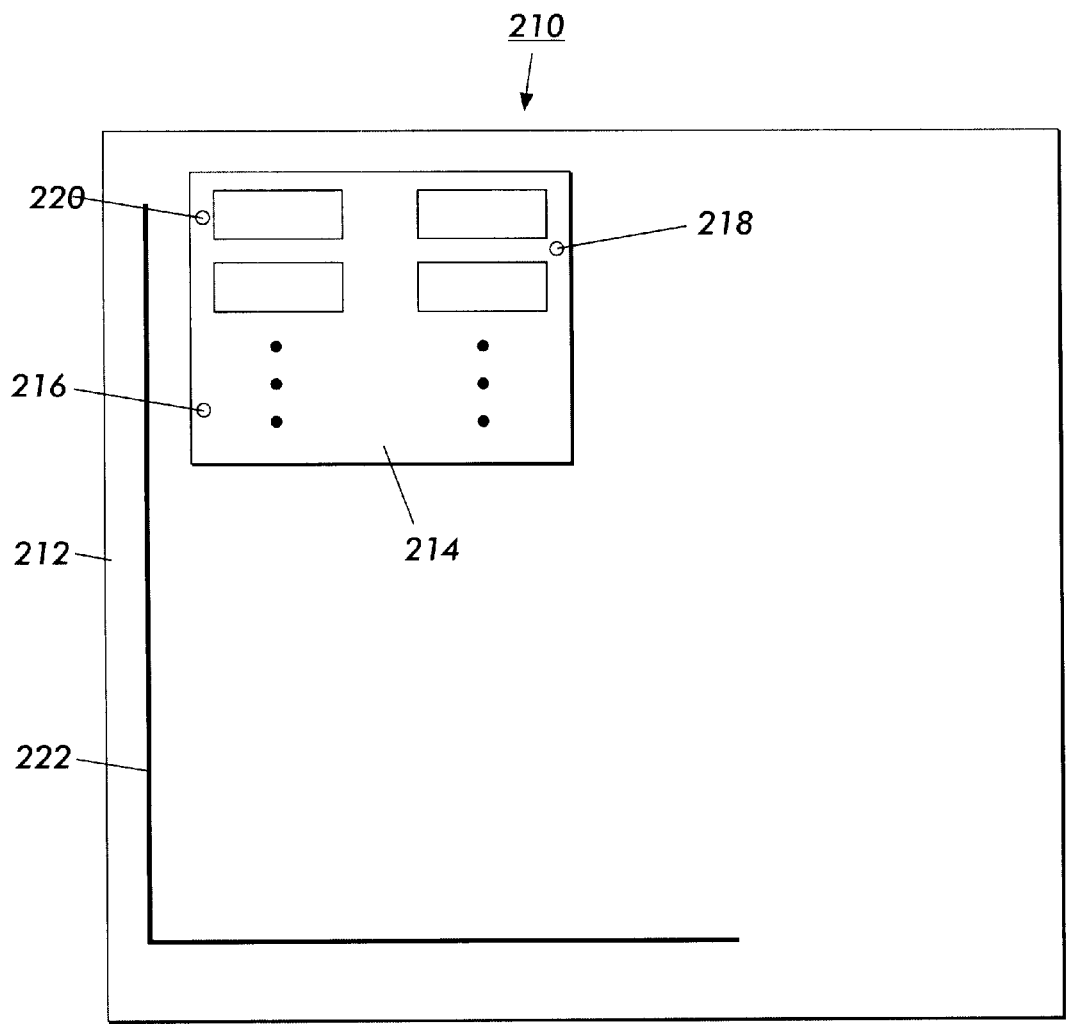
FIG. 12 depicts a front view of a multiple ejector system implementing sub-arrays of ejectors.

Turning to FIG. 12, illustrated is a top view of a further multiple ejector system 210. In this embodiment, rather than attaching individual drop ejection units, drop ejection subarrays, such as sub-array 214, are used. Specifically, multiple drop ejection units are configured on a single substrate, during for example, a drop ejection unit lithographic formation process. Using sub-arrays 214, requires fewer sets of tooling pins 216–220 on tooling plate 222. However, the same number of power connection and ground return connection pins as well as electrical tracings will be required. Additionally, using sub-arrays 214 increases the ease of handling the drop ejection units. Particularly, due to the small size of individual ejector units, handling these as individual units increases the complexity of the system as opposed to using the larger sub-arrays. Further, using the subarrays provides for more accurate alignment as a high degree of alignment accuracy may be obtained during the formation of the sub-array.

In order to increase the refinement of drop ejector positioner, connection pins such as those described in connection with FIGS. 10–12, are designed to have a certain flexibility built into the pin structure. This is beneficial, as this flexibility is useful for providing further fine alignment of the drop ejectors once connected to the pins. Thus, while the manufacturing process of the tooling plate and pins extending therefrom, as well as the connection holes on the drop ejectors are done with a high degree of precision, further alignment accuracy may be obtained if a spring or flexible capability is designed into the tooling pins. Such tooling pins allow for movement of the drop ejector in the horizontal X and Y plane such that the ejector is specifically aligned with a location for emitting. In an alternative embodiment, the through holes formed in the drop ejector units may be manufactured with a spring or flexible circumference, whereby firm engagement is made to the tooling pins, while also allowing for flexure in the X,Y horizontal range.

Further, the alignment grooves of the drop ejectors may be formed with a V groove or other design which allows for the movement of the pins for more precise alignment of the ejector. Such alignment elements and processings are known in the alignment field.

Additionally, while the embodiments previously shown discuss the use of three pins in the set of pins holding a drop ejector unit. It is to be understood that other arrangements of pin sets are possible. For example, in the proper situation, a 2-pin, 4-pin or other pin set arrangement may be most appropriate.

FIGS. 10 and 11 showed multiple ejector systems which use single-piece drop ejection units, both for piezoelectric drop ejection mechanisms and acoustic drop ejection mechanisms. Turning to FIGS. 13–16, set forth are side views of a section of multiple ejector system arrangements for two-piece piezoelectric drop ejection mechanisms and two-piece acoustic drop ejection mechanisms.

Figure 13:
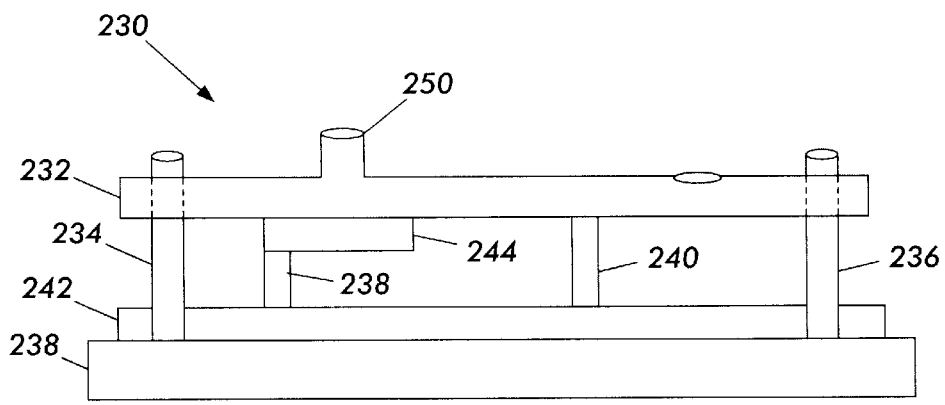
FIGS. 13 & 14 illustrate a single ejector in a multiple ejector system wherein the single ejector is a two-piece piezoelectric drop ejector unit.

FIG. 13 represents a side view of a multiple ejector system 230 and particularly a single ejector 232 of the system. Ejector 232 is connected to tooling pins 234 and 236. As in previous examples and for all following examples, there will also be an additional tooling pin, behind for example tooling pin 234, not seen in the figure. In this system 230 power connection pin 238 and ground return pin 240 extend from circuit board 242. Power connection pin 238 is in operative engagement with transducer 244, such that when power is supplied from controller or driver chip to power pin 238 via electrical tracings transducer 244 is activated causing ejection of droplets from nozzle 250.

Figure 14:
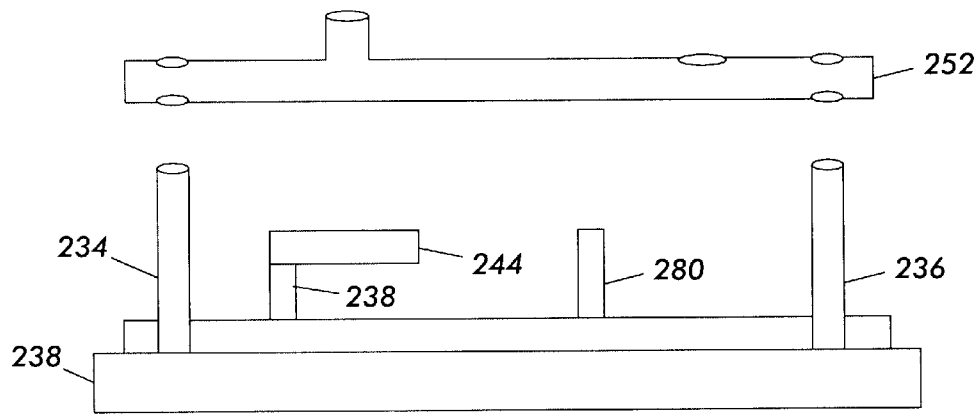

When the biofluid drop ejection unit of FIG. 13 is depleted, only the portion of the unit containing fluid is removed. The transducer portion as previously discussed will be maintained in the system. FIG. 14 illustrates this removal. Biofluid holding portion 252 has been removed from tooling pins 234 and 236. The transducer 244 is maintained in contact with power connection pin 238. Therefore, the connection between power connection pin 238 and transducer element 244 is semi-permanent.

Figure 15:
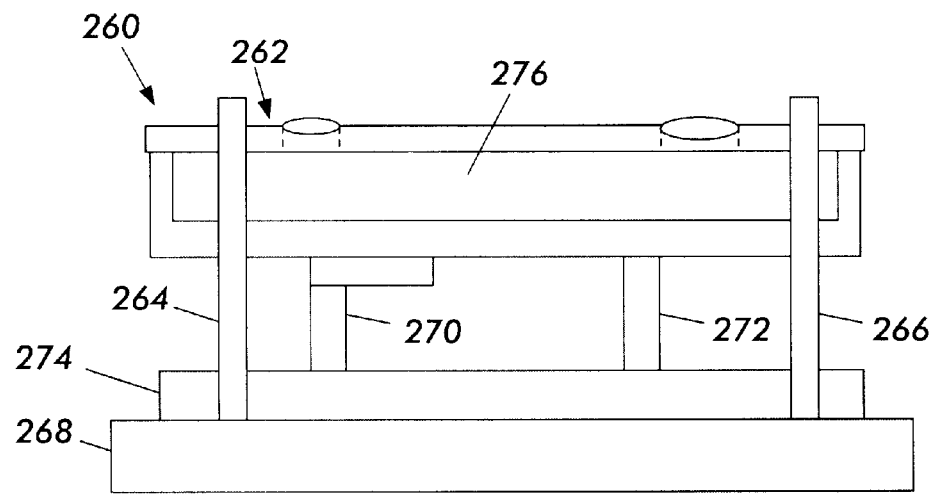
FIGS. 15 & 16 set forth a single ejector of a multiple ejector system wherein the ejector is a two-piece acoustic drop ejection mechanism.

Turning to FIGS. 15 and 16, a configuration for a multiple ejection system 260 using two-piece acoustic drop ejection mechanisms is illustrated. In FIG. 15, drop ejection mechanism 262 is in operative connection with appropriate tooling pins 264, 266 of tooling plate 268, power connection pin 270 and ground return pin 272 of circuit board 274, such that it is ready for operation. Once the biofluid held in cartridge 276 has been depleted, cartridge 276 is removed. FIG. 16 illustrates this situation. Upon removal of cartridge 276, the remaining portion of the acoustic drop ejection mechanism 262 which includes transducer/lens arrangement 277, is maintained in engagement with connecting pins 270 and 272.

In FIGS. 13–16, after the original biofluid cartridge is removed replacement biofluid cartridges can then be inserted into the system. The insertion of these replacement biofluid cartridges or holders may be accomplished by use of robots. It is noted that the forgoing systems may all be implemented using the sub-arrays of FIG. 12. Further, the alternative embodiments discussed in connection with FIGS. 10–12 are equally applicable to the arrangements of FIGS. 13–16.

As previously discussed, the present invention is a multiple ejector system having a large number of drop ejection units within a small area. The drops ejected are biofluids which are to be used in a biological assay. It is imperative for the intended use of the present invention, that the drops emitted are properly formed, properly placed and correspond to the locations of the intended emission. Since there will be a large number of different biofluids which may be used for a particular biological assay, it is important that there is an assurance the intended biofluid is located within the intended drop ejector. One particular manner of making sure biofluids within the MES are properly loaded, is to use fluorescent markers placed within the biofluid chambers of each drop ejector. The fluorescent markers are unique to a particular ejector such that the markers may be detected to insure that the proper fluid is being ejected from the proper ejector at the intended location.

Figure 17:
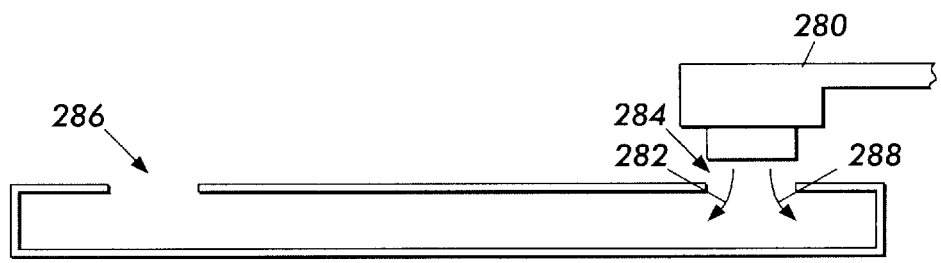
FIG. 17 sets forth a robotic filling technique for supplying biofluid.

Shown in FIG. 17 is a robotic filling system 280 which supplies biofluid 282 through a receiving port 284 of an ejector 286. It is noted that robotic system 280 is a simplified illustration. For example, system 280 would include separate dispensing heads to dispense the biofluid and the marker into an ejector. Robotic systems capable of dispensing many different substances into the ejectors are well known in the art. The filling operation may occur at the same location of printing or separate from this location. Specifically, the ejectors may be filled and then sent to the location of the multiple ejector system. Once they arrive they would then be loaded into the system. Alternatively, the ejectors may be loaded while in the multiple ejector system.

A quality control mechanism and process provided in the present application tests to determine that biofluids are actually deposited into drop ejectors.

Figure 18:
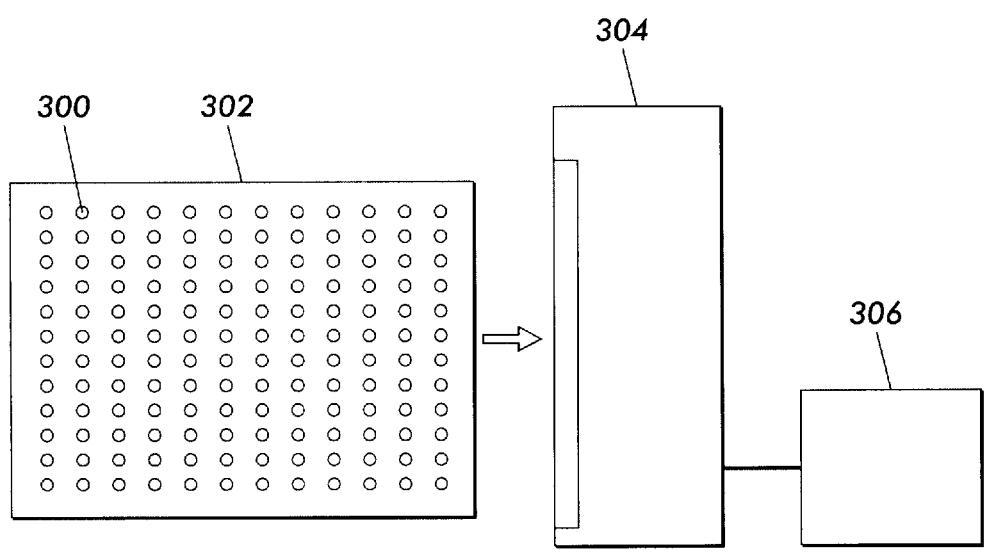
FIG. 18 depicts a pre-printing test strip according to the present invention.

One embodiment to accomplish this quality control occurs prior to the printing operation. Particularly, it has been noted that in certain embodiments a priming operation takes place. This concept was shown, for example, in FIG. 8 of the present application. The priming mechanism 144 applies a vacuum to pull biofluid from ejectors. During this operation a certain amount of biofluid contained within the ejection chambers is pulled up into at least a portion of the disposable elastomeric tubing 146 of FIG. 8. Therefore nozzle 142 and/or tubing 146 holds the small amount of fluid emitted during the priming operation. The robotic controlled priming mechanism is moved over a substrate such as 300 of FIG. 18, and the material in nozzle 142 and or tubing 146 is expelled by reversing the vacuum in order to emit this material onto substrate 300. In this manner, pre-operation droplets 302 are formed on substrate 300. It is noted that there can be a separate vacuuming nozzle 142 and disposable tubing 146 for each of the ejector units.

Substrate 300 is then be passed through an optical scanner system 304, which detects the existence or non-existence of a drop by known scanning operations. A controller 306, for example, may maintain a correlation table matching the location of a drop to a priming nozzle, which in turn is associated with a particular drop ejector unit. When a drop is not detected at the appropriate location, it is an indication that an ejector has been improperly loaded with biofluid or has not been properly primed.

In an alternative embodiment, the drops on substrate 300 may not be obtained through the use of the priming mechanism but rather after priming operations have taken place. In this embodiment, a test sample is printed and scanned prior to the printing of the biological assays. The pre-operational testing not only detects whether the ejectors are filled and primed, but also that each of the multitude of ejectors are operational. Particularly, if an individual ejector of an ejector printhead is not working, a drop will not be detected on the substrate where the spot should be located. This is an indication that the ejector is not loaded properly or properly primed. In either case the ejector of interest can then be more particularly investigated. Therefore, this pre-operation test may be used not only as verification of biofluid loading, but also that proper ejector operation is occurring.

In the foregoing embodiments all drop ejectors are tested to determine proper placement of biofluid and operation of drop ejectors. In another embodiment, a number less than each of the drop ejector units may be tested. Under this scenario, a sampling operation is taken to determine if the system is working. This sampling is less accurate than previous embodiments in the sense that it uses a statistical basis for operation as opposed to checking each ejector. A benefit of this operation is to increase testing speed.

Figure 19:
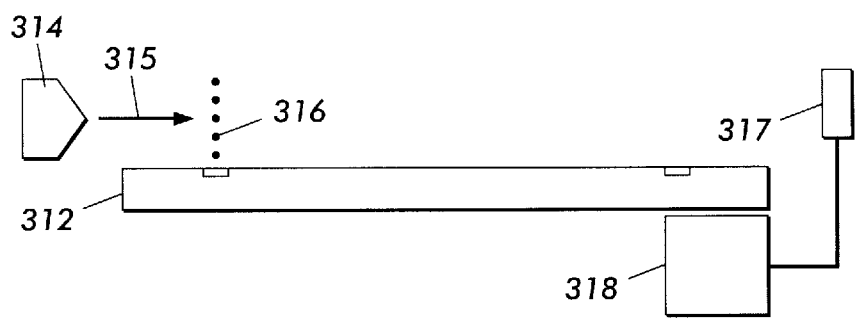
FIG. 19 illustrates a laser-scattering detector for operation of drop ejectors.

FIG. 19 proposes a further embodiment for detecting proper operation of ejectors such as ejector 312 in a multiple ejector system. Specifically, a laser 314 is positioned such that its laser beam 315 crosses droplets 316 emitted by ejector 312. A laser beam detector 317 is positioned to detect signals received from the laser 314. The present system provides a laser scattering operation of the drops in flight from ejector 312. Results of the detection from detector 317 is provided to controller 318. Controller 318 correlates which ejector is being tested to determine whether that ejector is properly operating. While the present figure illustrates a single ejector, it is to be understood that a multiple laser 314 and detector 317 system may be implemented to verify multiple ejectors at a single time. It is also to be appreciated that the multiple ejector system may be moved such that each ejector is tested, or alternatively the combination of the lasers 314 and detectors 317 may be moved across the multiple ejector system to ensure testing of each ejector. The variations of detecting mechanisms would be well known to one in the art.

As the presently described multiple ejector system is intended to operate with a multitude of drop ejector units ranging from 100 to 1,000 or more ejector units in a very small, compact space, verification of proper operation is a valuable benefit, to improve the quality and accuracy of drop placement. Therefore, while the forgoing embodiments are discussed as alternative embodiments, in certain situations, more than a single embodiment may be included in a system. This would increase the assurances that biofluid has been properly inserted into injectors, that the priming operations where appropriate have been undertaken, and that ejectors are in fact properly operating.

It is noted that the optical scanner 304 may in the embodiments disclosed provide simply a course review, i.e. in the priming testing embodiment, the specificity of drop location and formation is not of a high priority, only the existence of the biofluid material. On the other hand, a more refined scanning operation may be implemented with post-priming droplets to ensure not only the existence of the droplets, but a more precise verification as to their location, formation and size.

Figure 20:
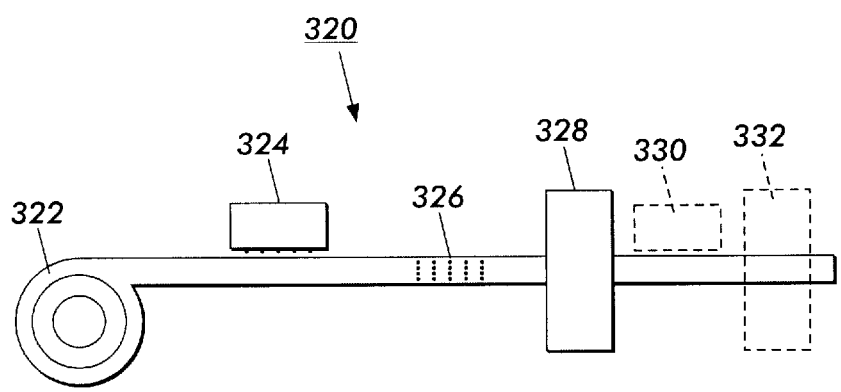
FIG. 20 illustrates a system according to the present invention.

Turning to FIG. 20, illustrated is an operational system 320 of the present invention. System 320 includes a substrate role 322, which may be a type of paper capable of receiving the biofluid drops. The substrate is moved through multiple ejector system 324 by known substrate handling mechanisms. The multiple ejector system 324 includes a plurality of ejectors arranged to deposit biofluid drops at predetermined locations on the moving substrate. In one embodiment, all of the ejectors may be constantly ejecting droplets onto the passing substrate, where the substrate speed is controlled to ensure proper placement of the drops to generate a biological assay 326. The biological assay is then passed through an optical scanner system 328. Under this design, each drop in the assay is tested to ensure both proper ejection operation. Thus where in previous embodiments testing of the multiple ejector system occurred prior to printing of the biological assay, the present embodiment tests each or some sub-set of each printed biological assay. The printed biological assays may then be held on the continuous roll 322, or may be individually separated into sheets.

The actual testing of biofluids on the printed substrate are intended to find some interaction between drops. Therefore, it is possible that ejector system 320 may eject more than a single drop on a single space. Alternatively, a further multiple ejection system 330 shown in dotted lines may be included in system 320 to provide the second set of drops. A further multiple ejector scanning system 332 may in this case also be included, to detect if the second drops have been properly ejected. Yet a further alternative when two or more multiple ejector systems has only a single scanning system provided after the last drops have been ejected.

It is to be appreciated that while the forgoing description sets forth embodiments for acoustic drop ejection units and piezoelectric drop ejection units, the concepts of the present invention may be equally extended to other drop ejection mechanisms and for fluid other than biofluids for which avoidance of contamination is beneficial.

It is to be further understood that while the figures in the above description illustrate the present invention, they are exemplary only. Others will recognize numerous modifications and adaptations of the illustrated embodiments which are in accord with the principles of the present invention. Therefore, the scope of the present invention is to be defined by the appended claims.

Having thus described the preferred embodiments, what is claimed is:

1. A multiple ejector system for printing arrays of biofluids, the multiple ejector system comprising: a tooling plate having a plurality of sets of tooling pins extending outward from a first surface of the tooling plate; a printed circuit board having at least a power connection extending from a surface of the circuit board; wherein said printed circuit board is placed on said first surface of the tooling plate; and a plurality of biofluid drop ejection units, each unit including alignment grooves and a transducer, each of the plurality of biofluid drop ejection units attached to at least a set of the tooling pins by connection to the alignment grooves.

2. The invention according to claim 1 wherein each of said plurality of sets of tooling pins comprises a power connection pin in operational connection with transducers of each associated drop ejection unit.

3. The invention according to claim 2 further including a plurality of ground return pins extending from the surface of the circuit board, and each of the plurality of ground return pins is connected to one of said drop ejection units.

4. The invention according to claim 2 wherein at least one of the tooling pins acts as a ground return.

5. The invention according to claim 3 wherein said power connection pins are in operational connection with respective transducers, and the ground return connection pins are in operational connection with a body portion of the drop ejection units.

6. The invention according to claim 1 wherein the tooling plate includes openings corresponding to the sets of tooling pins such that when the printed circuit board is brought into contact with a back surface of the tooling plate, the tooling pins pass through the tooling plate openings.

7. The invention according to claim 1 wherein the circuit board includes openings corresponding to the tooling pins such that when the tooling plate is brought into contact with a back surface of the circuit board, the tooling pins pass through the circuit board openings.

8. The invention according to claim 1 wherein the biofluid drop ejection unit for ejecting biofluid drops includes:

a biofluid containment area for holding a low volume of biofluid; and the transducer is integrated with the biofluid containment area as a single disposable unit, the transducer configured to eject drops of biofluid from the biofluid containment area.

9. The invention according to claim 1 wherein the biofluid drop ejection units are acoustic drop ejection units.

10. The invention according to claim 1 wherein the biofluid drop ejection units are piezoelectric drop ejection units.

11. The invention according to claim 5 wherein each of the drop ejection units are piezoelectric drop ejectors including:

the transducer being a piezo actuator;

a reagent cartridge having at least one surface with a first flexible membrane, which is in operative connection with the piezoelectric transducer; and a nozzle in operative connection with the reagent cartridge and positioned in relationship to the piezoelectric transducer such that action of the piezoelectric transducer causes the biofluid to be emitted through the nozzle as the biofluid drops.

12. The invention according to claim 2 wherein connection of the alignment grooves and tooling pins locates or aligns the drop ejection units to within one-thousandth of an inch of an ideal position.

13. The invention according to claim 1 wherein the multiple ejection system includes more than one hundred drop ejection units.

14. The invention according to claim 1 wherein different drop ejection units of the multiple drop ejection system contain different biofluids.

15. The invention according to claim 1 wherein the plurality of drop ejection units are formed as part of sub-arrays of drop ejector units.

16. The invention according to claim 1 wherein at least one of the tooling plate and tooling pins include drop ejector stops, wherein as the drop ejector moves past the tooling pins the stops act to hold the drop ejector at a predetermined position.

\* \* \* \* \*